United States Patent [19]

Kukes et al.

[11] Patent Number: 4,596,786

[45] Date of Patent: Jun. 24, 1986

[54] CALCINED AND REDUCED TITANIUM DIOXIDE ON SILICA-TUNGSTEN OXIDE CATALYST

[75] Inventors: Simon Kukes; Robert L. Banks, both of Bartlesville, Okla.

[73] Assignee: Phillips Petroleum Company, Bartlesville, Okla.

[21] Appl. No.: 710,809

[22] Filed: Mar. 12, 1985

Related U.S. Application Data

[62] Division of Ser. No. 580,402, Feb. 15, 1984.

[51] Int. Cl.$^4$ .................. B01J 21/08; B01J 21/06; B01J 23/30; C07C 6/00
[52] U.S. Cl. .................. 502/242; 502/254; 585/646
[58] Field of Search ............... 502/242, 254; 585/646, 585/643, 670

[56] References Cited

U.S. PATENT DOCUMENTS

| | | | |
|---|---|---|---|
| 3,261,879 | 7/1966 | Banks | 260/683 |
| 3,365,513 | 1/1968 | Heckelsberg | 585/643 |
| 3,418,390 | 12/1968 | Heckelsberg | 260/683 |
| 3,728,414 | 4/1973 | Van Helden et al. | 585/646 |
| 3,792,106 | 2/1974 | Regler | 260/683 D |
| 3,792,107 | 2/1974 | Fattore | 260/683 D |
| 4,269,737 | 5/1981 | Grenoble et al. | 502/242 |

FOREIGN PATENT DOCUMENTS 203020  12/1982  Japan .................. 502/254

*Primary Examiner*—P. E. Konopka
*Attorney, Agent, or Firm*—Howard D. Doescher

[57] ABSTRACT

Olefins are converted into other olefins having different numbers of carbon atoms by contact with a catalyst comprising a silica support containing tungsten oxide and a promoting amount of a least one titaniferous agent and activated under conditions suitable for the titaniferous agent to promote the activity of tungsten oxide and silica for the disproportionation and isomerization reaction.

11 Claims, No Drawings

CALCINED AND REDUCED TITANIUM DIOXIDE ON SILICA-TUNGSTEN OXIDE CATALYST

This application is a Division of application Ser. No. 580,402, now pending, filed Feb. 15, 1984.

BACKGROUND OF THE INVENTION

This invention relates to the conversion of olefins according to the olefin reaction, to catalysts therefore and to a method for modifying the activity of such catalysts. In accordance with one aspect, this invention relates to a catalyst comprising tungsten, silica and at least one titaniferous agent or component suitable for use in the disproportionation and isomerization of olefins.

In accordance with another aspect, this invention relates to a catalyst suitble for use in the disproportionation and isomerization of olefins comprising silica and tungsten promoted with at least one titaniferous agent or component.

In accordance with another aspect, this invention relates to a process for the disproportionation and isomerization of olefinic hydrocarbons with a disproportionation catalyst modified as hereinbefore described under conditions of temperature and pressure which effect disproportionation and isomerization of olefinic hydrocarbon feeds.

The disproportionation or metathesis of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene, and cis-, and trans-2-butene.

Another type of disproportionation involves the cross-disproportionation of two different olefins to form still other olefins. An example would be the reaction of one molecular of 2-butene with one molecule of 3-hexene to produce two molecules of 2-pentene.

By the term "disproportionation" or "metathesis" throughout the specification is meant the conversion of the feed olefinic (or unsaturated) hydrocarbon to a mixture of olefinic (or unsaturated) hydrocarbons having different numbers of carbon atoms than the feed hydrocarbons.

Among the catalysts that have been developed for disproportionation are those comprising silica containing a catalytic amount of tungsten oxide. The present invention is based upon the discovery of a way to improve the activity of such a catalyst for the isomerization of olefins.

Previously it has been found that the activity of olefin reaction catalysts, e.g. disproportionation or metathesis catalysts, can be modified by admixture with a double bond isomerization catalyst. For example, mixtures of olefin reaction catalysts with magnesium oxide or zinc oxide are particularly effective in increasing conversion and/or widening the spread of products.

It has now been found that the isomerization activity of an olefin reaction catalyst, i.e. a disproportionation or metathesis catalyst, can be modified by treating the catalyst with a titaniferous agent.

Accordingly, an object of this invention is to provide a method for the conversion of olefins.

Another object of this invention is to provide a catalyst for the conversion of olefins.

Still another object of this invention is to provide a method for converting olefins to olefins having different numbers of carbon atoms from the feed hydrocarbons.

Still another object of this invention is to provide a method for modifying the activity of a disproportionation catalyst for the isomerization of olefins.

Other aspects, objects, and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising silica containing a catalytically effective amount of tungsten is improved with respect to isomerization activity by contacting the catalyst with a promoting amount of at least one titaniferous agent or component under conditions suitable for the titaniferous agent to promote the isomerization activity of the tungsten-silica catalyst.

Further, in accordance with a specific embodiment of the present invention, a disproportionation (methathesis) catalyst comprising silica containing a catalytically effective amount of tungsten is modified by incorporating a promoting amount of least one titaniferous compound and then activating by heating under calcination and, optionally, reducing conditions suitable for the titaniferous compound to promote the isomerization activity of the tungsten-silica catalyst.

Also according to the invention, a process is provided for the disproportionation and isomerization of an olefinic hydrocarbon by contacting the same with a disproportionation catalyst modified as hereinbefore described under conditions of temperature and pressure which effect disproportionation and isomerization of the feed.

DESCRIPTION OF SPECIFIC EMBODIMENTS

The silica component of the catalyst can be any conventional catalyst-grade silica. Some examples are: precipitated silica gel, microspheroidal silica, flame hydrolyzed silica, and silica aero-gels. These materials have appreciable suface area, usually in the range of 50–700 $m^2$ per g and can range from fine powders to course granules. These materials often contain small amounts of compounds of aluminum and of sodium in the order of a few tenths of a percent by weight and smaller. Trace amounts of other metals and such small amounts of these materials are acceptable.

The tungsten component of the catalyst of the invention can be incorporated into the silica support by any suitable method including, for example, impregnation, dry mixing, and coprecipitation. Tungsten oxide can be added directly or in the form of a tungsten compound that can be converted to the oxide by calcination.

Generally the finished catalyst contains from about 0.1 to about 30 percent by weight of the tungsten component calculated as the metal oxide and based on the total weight of the tungsten component and the silica component, although larger amounts can be used. In most instances a proper amount of the promoter is from about 1 to about 20 percent. Excellent results have been obtained with silica-based catalysts containing from about 2 to about 15 percent by weight of tungsten oxide.

The solid component of the catalyst can be in any conventional catalytic shape or size depending upon the type of conversion in which it is to be utilized. For example, in fixed-bed catalyst systems the solid composite can be in the form of spheres, pellets, extrudates, agglomerates, and the like. In slurry-catalyst systems, the solid can be in the form of relatively small particles or in the form of a powder.

According to the invention, a tungsten-silica olefin reaction catalyst is modified by the inclusion of a titaniferous compound deposited on the surface thereof. The titaniferous compound is deposited on the surface of the catalyst by impregnation, coprecipitation, or other suitable means. The titaniferous compound can be incorporated as titanium(IV) oxide or as a compound convertible to titanium(IV) oxide by calcination. The titaniferous compound can be incorporated before, at the same time, or after the incorporation of the tungsten compound into the silica support.

Representative examples of suitable titaniferous compounds (containing or yielding titanium) that can be used include:

Titanium(IV) oxide;
Titanium alkoxides of the general formula Ti(OR)$_4$, where R is hydrocarbyl, for example, titanium(IV) n-propoxide, titanium IV isopropoxide, titanium(IV) ethoxide, titanium(IV) n-butoxide, titanium(IV) 2-ethylhexoxide;
Titanium carboxylates such as titanium(IV) oxalate, titanium(IV) citrate, titanium(IV) cresylate;
Titanium acetylacetonate;
Titanium chelates, particularly alkanolamine titanates, e.g., triethanolamine titanate, triethanolamine titanate chelate having the formula

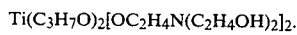

Ti(C$_3$H$_7$O)$_2$[OC$_2$H$_4$N(C$_2$H$_4$OH)$_2$]$_2$.

(This is available from DuPont under the designation Tyzor TE);
Titanium halides, such as titanium(III) chloride, and titanium(IV) chloride,
and the like, and mixtures thereof.

Generally, the finished catalyst contains from about 0.1 to about 20, preferably from about 1 to about 10 weight percent of the titanium component calculated as titanium dioxide and based on the total weight of the tungsten oxide and the silica support.

To be effective in the present catalyst system, the above described components of the catalysts are activated at elevated temperatures, generally in flowing air. The activation or calcination of the catalyst is accomplished at a temperature of from about 300° C. to about 800° C. for a period of about several minutes to several hours or longer. A convenient and economical treatment is a temperature in the range of about 400°-700° C. for 0.5 to about 20 hours or longer.

The calcined catalyst described above can be, if desired, further subjected to a high temperature treatment in a reducing atmosphere. The temperature range and temperature of contact can be the same as used for calcination with a treating gas such as carbon monoxide, hydrogen, and the like. The activated catalyst is preferably cooled with an inert gas such as nitrogen prior to use in the olefin reaction.

The promoted catalyst can be used in disproportionation reactions in a conventional manner. The reaction temperature can vary depending upon the catalyst and feed(s) employed, but will be sufficient to effect disproportionation. Typically, the disproportionation is carried out at a temperature in the range of about 20° to about 600° C.

The disproportionation reaction can be carried out by contacting the olefins to be disproportionated with the catalyst in the liquid phase or the gas phase, depending on structure and molecular weight of the olefins, temperature and pressure.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3-30 carbon atoms per molecule and with such cyclic olefins having 4-30 carbon atoms per molecule. Nontertiary olefins are those olefins wherein each carbon atom, which is attached to another carbon atom by means of a double bond, is also attached to at least one hydrogen atom. Internal olefins are preferred.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexene, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethylcyclooctadiene-1,4, and the like, and mixtures thereof.

The pressure during the disproportionation reaction may vary between wide limits. Pressures between 0.1 and 500 atm. are suitable; preferred pressures are between 0.5 and 250 atm. If possible, the process should be operated at a pressure which is atmospheric or nearly atmospheric so that no vacuum or pressure apparatus is required.

If the reaction is carried out in the liquid phase, solvents or diluents for the reactants may be used. Aliphatic saturated hydrocarbons (e.g., pentane, hexane, cyclohexane, dodecane) and aromatic hydrocarbons such as benzene and toluene are suitable. If the reaction is carried out in the gaseous phase, diluents such as aliphatic hydrocarbons (e.g., methane, ethane) and/or inert gases (e.g., nitrogen, argon) can be present. Preferably the disproportionation reaction is effected in the substantial absence of reactive materials such as water and oxygen.

The length of time during which the olefinically unsaturated compounds to be disproportionated are contacted with the catalyst depends upon several factors such as the activity of the catalyst, temperature, pressure, and structure of the olefinically unsaturated compound to be disproportionated. Contact time can conveniently vary between 0.1 second and 24 hours, although longer and shorter contact times may be used. The contact time needed do obtain a reasonable yield of disproportionated products depends on the factors mentioned above.

The process of the invention is effected batchwise or continuously, with fixed catalyst beds, slurried catalysts, fluidized beds or by using any other conventional contacting technique. The solid disproportionation catalysts are employed in any appropriate form, for example, as powders, flakes, pellets, spheres or extrudates.

The olefinic products of the invention, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

The following examples illustrate the invention.

EXAMPLE 1

Control catalyst preparation 2.31 g ammonium metatungstate dissolved in 77 mL water was used to impregnate 33 g silica (20–40 mesh size, low sodium, low alumina). The water was evaporated in air as the catalyst was dried over a hot plate. The material was then calcined in air at 500° C. to produce 6 wt% $WO_3/SiO_2$ catalyst.

Inventive catalyst preparation 10 mL of a 1 molar aqueous solution of titanium (IV) citrate and 0.82 g ammonium metatungstate dissolved in 50 mL water were combined and added to 11.2 g silica. The catalyst was dried as above to produce 6 wt% $TiO_2$/6 wt % $WO_3/SiO_2$ catalyst.

Comparative Catalytic Tests

Tests for disproportionation/isomerization activity with propylene feed were run in a quartz tube reactor with 1.5 g of catalyst supported by quartz wool in the center of the reactor which was heated in an electric furnace.

Identical runs were made with the 6% $WO_3/SiO_2$ control catalyst and with the 6% $TiO_2$/6% $WO_3/SiO_2$ inventive catalyst described above. Each catalyst was heated 1 hr at 600° C. with air flowing at 200 mL/min, then ½ hr with nitrogen flowing at 200 mL/min then the temperature was lowered to 400° C. to begin the test. Both runs were made with polymerization grade propylene fed at 150 mL/min at atmospheric pressure. The catalyst temperature was maintained at 400° C. Effluent from the reactor was analyzed with a gas chromatograph. Several samples were taken during the 1½ hr test for analyses. Averages for these analyses are presented in Table I.

TABLE I

| Catalyst | Propylene Conversion, % | Selectivity to 1-butene, % |
|---|---|---|
| 6% $WO_3/SiO_2$ | 16.6 | 0.6 |
| 6% $TiO_2$/6% $WO_3/SiO_2$ | 21.1 | 10.3 |

The field of 1-butene provides a measure of the double bond isomerization activity of the catalyst. Ethylene and 2-butene are the primary products of propylene disproportionation, and the 1-butene is produced by isomerization of the 2-butene. Selectivity to produce 1-butene with the inventive catalyst was much greater than with the control.

EXAMPLE 2

Control Catalyst preparation

Following a procedure similar to that of example I, a 10 wt% $WO_3/SiO_2$ catalyst was prepared. This is designated Catalyst 1.

Inventive catalyst preparation

The same silica base used above was impregnated with an aqueous solution of bis(triethanolamine)-titanium diisopropoxide (Tyzor TE, a product of E. I. du Pont de Nemours & Co., Inc. Wilmington, DE). The impregnated silica was dried at 400° C. for 1 hr. After cooling, the titanium-impregnated silica was further impregnated with ammonium metatungstate. After drying in air at 250° C. for 1 hr, the catalyst contained about 10 wt% tungsten oxide and 8 wt% titanium oxide on silica. This is designated Catalyst 2.

Comparative Catalytic Tests

Tests for disproportionation/isomerization activity with 1-hexene were run in a vertical stainless steel tube reactor, 3/4" o.d.×14" long. Glass wool and glass beads were used to position the fixed bed of catalysts in the center of the reactor which was heated in an electric furnace.

Comparative runs were made with the 10% $WO_3/SiO_2$ control catalyst and with the 8% $TiO_2$/10% $WO_3/SiO_2$ catalyst described above. For each run, 0.7 g catalyst was activated by heating the bed at 550° C. in flowing air for 2 hr., then in CO for 30 min and cooling under argon flow to reaction test temperature. Both runs were made with 1-hexene purified by pumping it through beds of silica gel and MgO prior to entering the heated reactor. In each six hour run the reaction temperature was increased at one hour intervals. The pressure in the reactor was 50 psig. The results are presented in the following table II.

TABLE II

| Run | Catalyst | Temp. (°C.) | WHSV* | 1-hexene Conv. % | Selectivity $C_{10}$ olefins, % | $C_5^=$ | $C_6^=$ | $C_7^=$ | $C_8^=$ | $C_9^=$ | $C_{10}^=$ | $C_{11}^=$ | $C_{12}^=$ |
|---|---|---|---|---|---|---|---|---|---|---|---|---|---|
| 1 | 10% $WO_3/SiO_2$ | 298 | 40 | 11.2 | 75.5 | 0.6 | 88.8 | 0.8 | 0.2 | 0.6 | 8.46 | 0.2 | 0.04 |
| 2 | 8% $TiO_2$/10% $WO_3/SiO_2$ | 296 | 41 | 14.8 | 43.2 | 1.8 | 85.2 | 2.4 | 1.0 | 1.9 | 6.4 | 0.5 | 0.1 |
| 3 | 10% $WO_3/SiO_2$ | 350 | 39 | 34.5 | 62.7 | 2.2 | 65.5 | 3.3 | 1.2 | 3.2 | 21.6 | 1.6 | 0.4 |
| 4 | 8% $TiO_2$/10% $WO_3/SiO_2$ | 352 | 40 | 32.2 | 31.1 | 4.3 | 67.9 | 5.7 | 3.0 | 4.6 | 10.0 | 1.6 | 0.5 |
| 5 | 10% $WO_3/SiO_2$ | 353 | 80 | 15.6 | 74.7 | 0.8 | 84.4 | 1.0 | 0.3 | 0.9 | 11.7 | 0.4 | 0.05 |
| 6 | 8% $TiO_2$/10% $WO_3/SiO_2$ | 348 | 78 | 20.4 | 43.5 | 2.3 | 79.6 | 3.1 | 1.3 | 2.6 | 8.9 | 0.9 | 0.3 |

TABLE II-continued

| Run | Catalyst | Temp. (°C.) | WHSV* | 1-hexene Conv. % | Selectivity $C_{10}$ olefins, % | Liquid Product Distribution (mole %) | | | | | | | |
| --- | --- | --- | --- | --- | --- | --- | --- | --- | --- | --- | --- | --- | --- |
| | | | | | | $C_5^=$ | $C_6^=$ | $C_7^=$ | $C_8^=$ | $C_9^=$ | $C_{10}^=$ | $C_{11}^=$ | $C_{12}^=$ |
| 7 | 10% $WO_3/SiO_2$ | 397 | 41 | 47.7 | 48.7 | 4.1 | 52.3 | 6.3 | 2.8 | 5.9 | 23.2 | 2.8 | 0.7 |
| 8 | 8% $TiO_2$/10% $WO_3/SiO_2$ | 397 | 40 | 52.5 | 25.2 | 6.5 | 47.5 | 9.9 | 6.1 | 8.2 | 13.2 | 3.2 | 1.2 |
| 9 | 10% $WO_3/SiO_2$ | 402 | 82 | 34.9 | 61.7 | 2.4 | 65.1 | 3.4 | 1.2 | 3.3 | 21.5 | 1.5 | 0.3 |
| 10 | 8% $TiO_2$/10% $WO_3/SiO_2$ | 403 | 82 | 35.6 | 35.9 | 4.2 | 64.5 | 5.9 | 2.9 | 5.1 | 12.8 | 1.9 | 0.6 |
| 11 | 10% $WO_3/SiO_2$ | 449 | 81 | 49.0 | 45.3 | 4.5 | 51.0 | 7.1 | 3.2 | 6.4 | 22.2 | 2.8 | 0.6 |
| 12 | 8% $TiO_2$/10% $WO_3/SiO_2$ | 451 | 80 | 45.3 | 36.4 | 4.7 | 54.7 | 7.4 | 3.9 | 6.5 | 16.5 | 2.7 | 0.7 |

*gm 1-hexene/gm catalyst/hr (feed rate)

Inspection of Table II shows that $TiO_2/WO_3/SiO_2$ catalyst causes generally higher conversion of 1-hexene than does the $WO_3/SiO_2$ catalyst. Ethylene and 5-decene are the primary products of 1-hexene disproportionation. Thus data in Table II show for the $WO_3/SiO_2$ catalyst that $C_{10}$ olefin is the major product. The other $C_5$ through $C_{12}$ liquid olefins produced are a result of isomerization. Comparison of the data for the inventive catalyst to the control shows higher amounts of $C_5$, $C_7$, $C_8$, $C_9$, $C_{11}$ and $C_{12}$ indicating enhanced isomerization with the titanated $WO_3/SiO_2$ catalyst.

We claim:

1. An activated calcined and carbon monoxide or hydrogen reduced composition suitable for the disproportionation and isomerization of olefins consisting of an effective promoting amount of titanium dioxide said titanium dioxide or titanium compound that is converted to titanium dioxide by calcination having been precipitated on the surface of a silica-tungsten oxide mixture and subsequently having been subjected to conditions of (1) calcination, and (2) reduction in a carbon monoxide or hydrogen atmosphere.

2. A composition according to claim 1 wherein said catalytic amount of tungsten oxide is in the range of about 0.1 to about 30 percent by weight of the combined weights of tungsten oxide and silica.

3. A composition according to claim 2 wherein said titanium dioxide or titanium compound that is converted to titanium dioxide by calcination is employed in an amount in the range of about 1 to about 10 weight percent of the titanium compound calculated as titanium dioxide based on the weight of tungsten oxide-silica combination.

4. An activated calcined and carbon monoxide reduced catalyst suitable for the disproportionation and isomerization of olefins consisting of a mixture of silica and about 1 to about 20 weight percent tungsten oxide upon which mixture is precipitated about 0.1 to about 20 weight percent of titanium dioxide, said amounts being based on the combined weights of tungsten oxide and silica.

5. A composition according to claim 4 wherein the amount of titanium dioxide present ranges from about 1 to about 10 weight percent.

6. A process for preparing a catalyst consisting essentially of silica, tungsten oxide, and titanium dioxide which is active for the disproportionation and isomerization of olefins comprising (1) admixing a catalytically effective amount of tungsten oxide and a silica support to provide a first composition of silica-tungsten oxide, (2) precipitating on the surface of said silica-tungsten oxide mixture a promoting amount of titanium dioxide or a titanium compound that is converted to titanium dioxide by calcination to provide a second composition and (3) subjecting said second composition to calcination to produce a calcined composition and (4) subjecting said calcined composition to reducing conditions suitable for promoting the activity of said composition for the disproportionation and isomerization of olefins.

7. A process according to claim 6 wherein said titanium dioxide or titanium compound is added in solution to silica containing tungsten oxide and the resulting composition is heated to an elevated temperature of from about 300° C. to about 800° C. under calcination conditions followed by reducing conditions at an elevated temperature with a treating gas comprising carbon monoxide or hydrogen sufficient to activate the catalyst.

8. A process according to claim 7 wherein said catalytic amount of tungsten oxide is in the range of about 0.1 to about 30 percent of the combined weights of tungsten oxide and silica.

9. A process according to claim 8 wherein titanium compound is employed in an amount in the range of about 0.1 to about 20 weight percent of said titanium compound calculated as titanium dioxide based on the weight of tungsten oxide-silica combination.

10. A process according to claim 9 wherein said titanium compound is titanium (IV) citrate or bis(triethanolamine)titanium diisopropoxide.

11. A process according to claim 7 wherein said calcination and reducing treatments are carried out at about the same elevated temperature.

* * * * *